United States Patent [19]

Kraus

[11] 4,214,092

[45] Jul. 22, 1980

[54] REARRANGEMENT OF ACYLOXY FURANS AND THIOPHENES PREPARED FROM BUTENOLIDES

[75] Inventor: George A. Kraus, Ames, Iowa

[73] Assignee: Iowa State University Research Foundation, Inc., Ames, Iowa

[21] Appl. No.: 13,519

[22] Filed: Feb. 21, 1979

[51] Int. Cl.$^2$ .................. C07D 333/16; C07D 307/12
[52] U.S. Cl. .................................... 549/64; 260/347.8
[58] Field of Search ...................... 260/332.3 C, 347.8; 549/64

[56] References Cited

PUBLICATIONS

Olah "Friedel-Crafts & Related Reactions" vol. 1 (1963), pp. 100,101.
Weininger "Contemporary Organic Chemistry" (1972), pp. 404,405.

*Primary Examiner*—Alan Siegel
*Attorney, Agent, or Firm*—Zarley, McKee, Thomte, Voorhees & Sease

[57] ABSTRACT

A method of preparing acyloxy furans and thiophenes from butenolides comprising reacting a pre-selected butenolide with an acylating agent in the presence of a base to provide an acyloxy furan intermediate, which in turn undergoes rearrangement in the presence of Lewis Acids by cleavage of a carbon-oxygen bond, and addition of the cleaved moiety to the furan ring forming a carbon-carbon bond on the ring. The result is a heretofore unknown group of lactone type compounds which are biologically active, in and of themselves, and in addition offer use as versatile synthesis intermediates to achieve, by conventional synthesis methods heretofore unavailable compounds.

9 Claims, No Drawings

REARRANGEMENT OF ACYLOXY FURANS AND THIOPHENES PREPARED FROM BUTENOLIDES

GRANT REFERENCE

The invention described herein was made in the course of work under a grant or award from the Department of Health Education and Welfare.

BACKGROUND OF THE INVENTION

This invention relates to preparation of acyloxy furans and thiophenes which undergo rearrangement in the presence of Lewis acids, using as starting materials butenolides. Prior to this invention, and my invention disclosed and claimed in co-pending U.S. application Ser. No. 966,268, entitled ALKOXY OR ACYLOXY FURANS FROM BUTENOLIDES, field Dec. 4, 1978, there has been no reasonable synthetic method for the general preparation of acyloxy furans. In my prior application, the butenolide ring is first treated with alkylating agents, such as trialkyl chlorosilanes in the presence of a strong organic base, and thereafter the alkylated furan ring is reacted with an organic electrophile to provide addition of the electrophile to the alpha position of the furan ring.

In accordance with the present invention in the first step of the reaction, acylating agents are utilized. It has been discovered that when acylating agents are employed in the first step reaction synthesis, followed by a catalytic reaction with Lewis acids, a novel and unexpected arrangement to form compounds of the class known as keto-lactones are prepared. These compounds have been previously unreported in the literature and offer avenues to synthesis of a wide variety of active compounds.

As those skilled in the art know and understand, furan compounds are those which contain at some point in the compound's structure the following common nucleus:

Such furan ring containing compounds are valuable precursors for the preparation of a wide variety of biologically active compounds. They can, for example, be successfully used as the starting point for preparation of complex butenolides, of other substituted furans, and they can be used for the making of such biologically active compounds, such as lycorine which is an antibacterial agent whose structure represents a challenge to present methods of synthesis, gibberelic acid, which is an important plant growth regulator that is not easily available from natural sources, and protoanemonin and its substituted derivatives, among others. In short, the number of desirable biologically active compounds which can be prepared using as a nucleus the furan moiety is almost limitless.

However, the effective utilization of furans as a precursor for preparation the numerous desirable biologically active compounds such as those listed above has met with only limited success and usage in the past. This is so primarily because of the difficulty of obtaining the furan starting materials.

Accordingly a primary object of this invention is to provide a synthesis process which allows for quick, easy high yield preparation of furan compounds.

Another object of the invention is to provide a synthetic process for preparation of furans which in turn can be used as building blocks for preparing a wide variety of biologically active compounds.

Yet another object of this invention is to provide an intermediate class of furans which are prepared from readily available butenolides as a starting material and which under the conditions of the reaction of this invention, undergo rearrangement to provide an intermediate furan ring. The intermediate furan ring itself is then reacted in the presence of catalytically effective amounts of Lewis acids to provide an additional rearrangement which is unexpected, unreported in the literature, and provides not only novel compounds, but novel compounds which are highly useful biologically active compounds in and of themselves; and which further can, in turn, be used as starting materials to achieve synthesis of a wide variety of compounds which previously have not been available by conventional laboratory synthesis.

The method and manner of accomplishing these objects of the invention, as well as others, will become apparent from the detailed description of the invention which follows.

SUMMARY OF THE INVENTION

A butenolide or substituted butenolide is reacted with an acylating agent such as acetylchloride, in the presence of a base and suitable organic solvent, to provide an acylated furan ring containing intermediate. The intermediate in turn is reacted in the presence of a catalytically effective amount of a Lewis acid to provide clevage of the added acyl moiety at a carbon-oxygen bond and addition of the cleved moiety to another position on the ring.

DETAILED DESCRIPTION OF THE INVENTION

In accordance with the first step of the process of this invention, a butenolide of the following formula is the starting material:

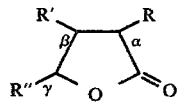

As can be seen, the starting butenolide may if desired be substituted at the alpha, beta, and gamma positions. R, R' and R" can be selected from the group consisting of hydrogen, and nonfunctionally substituted alkyls, alkenyls, alknyls and aryls. The R, R' and R" moieties must be non-functionally substituted in order to prevent undesired side reactions from occurring on these side chain moieties, as opposed to undergoing the desired furan rearrangement. For example, it has been found that if either R, R' or R" is substituted with the carbomethoxy group, the reaction fails. Preferably R, R' and R" are $C_1$ to $C_{12}$ substituents.

As explained hereinafter in more detail, if one desires to prepare thiophenes, the starting butenolide ring will have a sulfur atom in place of the oxygen moiety in the ring providing the following ring structure:

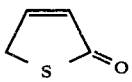

In the remaining portion of the disclosure, the reaction of the thioderivatives should be assumed to be the same as the oxygen containing rings, unless specifically stated to the contrary.

The butenolide in the first step reaction is reacted with an acylating agent of the following formula:

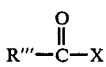

"X" represents any halide. It is, however, most preferably chloride. R''' represents any of the same groups as previously discussed for R, R' and R''. Of course, it is preferred that the acylating agent be a chloride, because of ease of availability, ease of preparation and predictability of formation and reaction.

The butenolide and the acylating agent are reacted together in the presence of a base and a substantially inert solvent. The solvent maybe any anhydrous inert solvent such as ether, tetrahydrofuran, or dimethoxyethane, commonly referred to as glyme.

The purpose of the base is to remove a proton from the butenolide ring. Suitable bases are well known and the workup for such bases is also well known in the art. Bases which will work in the reaction of this invention are preferably the dialkylamde bases which are formed by the reaction of alkyl lithium and dialkyl amines. Preferably the alkyl group is $C_2$ or greater. For example, tertiarybutyllithium with a compound such as disopropyl amine may be dissolved in tetrohydrofuran (THF) and hexamethylphosphoric triamide (HMPA) to provide a base such as di-isopropyl lithium amide represented by the following formula:

Preparation of the bases suitable for reaction in this invention is well known and will not be described in detail. For further reference to the preparation of bases, see for example J. American Chemical Society, 89 (1967) at pages 2500 through 2503 which is incorporated herein by reference.

Since the reaction ingredients for this reaction are highly reactive, it is preferable, and in most cases essential that the reaction be conducted in an inert atmosphere such as an argon or nitrogen atmosphere. Any oxygen which is present will react with the base and the intermediate carbanion which is formed. It is for this reason that the system is flushed with an inert gas.

The reaction of the butenolide and the preferred acylating agent, in the presence of a base will provide addition of the acylating agent on the butenolide ring and rearrangement to a furan ring. The resulting intermediate compound has the following formula.

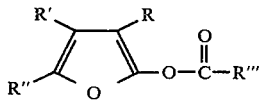

It has been found most desirable and efficient when equimolar quantities of all reactants are employed. Reaction temperatures likewise are not critical, although it has been found desirable to react at room temperature, or lower. Pressure does not appear to be a controlling factor. Atmospheric pressure works satisfactorily.

As can be seen from the structural formula presented for the acylated compound, there is a rearrangement from the butenolide ring formation in the initial starting reactant to the furan ring arrangement. The intermediate acylated compound is next reacted, in the presence of a Lewis acid to provide yet another rearrangement which results in the formation of the novel ketolactone compounds preferred by the process of the inventor.

Reference is made to the immediately preceding structural formula for the furan ring containing intermedite. As can be seen, the acyl group of the acylating agent adds to the carbonyl group of the furan ring forming an oxygen-carbon bond. In the rearrangement which occurs in the presence of a Lewis acid, the oxygen-carbon bond is broken and the butenolide ring again forms with the remaining portion of the acyl moiety attaching to the ring at the gamma position. The reaction is represented by the following equation:

[See immediately preceding structure] 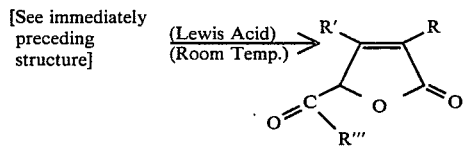

As can be seen in the reaction, the furan ring is once again converted to the basic butenolide ring with the additional rearrangement previously described. The resulting compound is a keto lactone as depicted schematically on the right hand side of the equation. This class of keto lactones is novel and has not heretofore been prepared.

The Lewis acids which may be utilized are any of the conventional well known Lewis acids. For example, boron trifluoride, stannic chloride, aluminum chloride, titanium tetrachloride, zinc chloride, and boron trichloride. The amount of the Lewis acid used as shown in the examples which follow is an equivalent amount. However, since the reaction is a catalytic one without the Lewis acid itself entering into the reaction, amounts as low as traditional catalytically effective amounts may be employed. Satisfactory results may be achieved with amounts varying from 10% of an equivalent of the Lewis acid up to equal molar amounts.

The reaction must be conducted in an anhydrous solvent since water will destroy the catalytic effectiveness of the Lewis acid. Suitable solvents for employment in reactions utilizing Lewis acids are well known and need not be described herein in detail. Generally, very satisfactory results are achieved with chlorocarbon solvents such as methylene chloride, trichloromethane, and carbon tetrachloride. Other hydrocarbon solvents such as hexane and pentane will work equally satisfactorily. Ether solvents such as ether itself and tetrahydrofuran are also suitable. The important criteria in selecting the solvent is that it must be stable with respect to the Lewis acid. Additionally, it must not interact with the furan intermediate formed in the first step of the reaction synthesis. Other substantially inert organic solvents which may be used would include acetonitrile as well as others.

The Lewis acid catalyzed rearrangement does not appear temperature or pressure sensitive. It may be conducted at room temperature as well as temperatures above and below room temperature. The reaction is likewise not sensitive to pressure and may be conducted conveniently at atmospheric pressure.

The novel keto lactone type compounds formed all contain the butenolide ring and like all butenolides, are known to be biologically active. For example, they are capable of adding cysteine, an essential amino acid. This fact alone indicates biological complexing. Some of the compounds prepared have been tested and it has been found that they have considerable value as plant growth inhibitors.

In this regard, the Examiner's attention is directed to Example One below. Other of the novel compounds prepared in accordance with the process of this invention are suspected as being effective herbicides, plant growth regulators, yield enhancers, fungicides, insecticides, miticides, insect growth regulators and humaticides. Testing for these specific uses and overall effectiveness is now commencing.

The following examples show preparation of acyloxy furans which undergo the rearrangement of this invention to provide keto lactones containing the butenolide ring. Representative examples are shown both in the acyloxy furan arrangement and the thiophene rearrangement. The examples which are shown illustrate the synthesis and scope of the invention, but are not intended as limiting.

EXAMPLES

(General Procedure Description)

In each of the following examples, the appropriate starting material butenolide was reacted with the specified acylating agent in the first step reaction synthesis, in tetrahydrofuran solvent in the presence of i—Pr$_2$HLi and hexamethyl phosphoric triamide to provide an intermediate furan ring containing compound of the general formula previously specified. The amounts of each ingredient were equimolar and the reaction was run at atmospheric pressure, under a nitrogen atmosphere. Cooling of the reaction was by a dry ice acetone bath.

The first step reaction was conducted at $-78°$ C. initially and allowed to gradually warm to $0°$ C. The ingredients were added in the following manner: The starting butenolide was added to the tetrahydrofuran solvent which in turn was added to the lithium di-iso-propyl-amide-HMPA complex at $-78°$ over a 10 minute period. Stirring continued for 20 minutes and then the acylating agent was added rapidly, with stirring continuing for an additional 10 minutes at $-78°$ C. and then for an additional 60 minutes at $0°$ C. After the 60 minute time interval the reaction mixtuure was poured into approximately 200 milliliters of hexane. The organic layer, which separated, was washed twice with 50 milliliters of water and once with a 25 milliliter of brine solution followed by drying with sodium sulfate. It was thereafter filtered and rotor evaporated. Chromatography analysis was conducted to reveal the specified percent yield of desired furan ring containing intermediate compounds. In each instance, these general conditions were employed except to the extent modifications are noted.

Thereafter, the separated intermediate was utilized in the second step rearrangement reaction procedure with the appropriate Lewis acid, as specified in the examples, to provide the second rearrangement resulting in the reformation of the butenolide ring and the appropriate keto lactone compound. Conditions for the second step of the reaction are individually specified in the examples below.

EXAMPLE 1

Angelicalactone R equals hydrogen, R' equals hydrogen and R" equals methyl was used as the starting butenolide. It was reacted in the first step with acetylchloride (R'" I CH$_3$) under the general conditions specified above. In particular, a solution of 10 mmol of angelicalactone in 5 mL of tetrahydrofuran (THF) was added over 5 minutes to a solution of 11 mmol of lithium diisopropylamide in 10 ml of THF at $-78°$ C. The solution was stirred at $-78°$ C. for 15 minutes. The acetyl acid chloride (20 mmol) was added rapidly and the resulting suspension was stirred an additional 5 minutes. The reaction was worked up by the addition of ether and water. The aqueous layer was extracted twice with ether. The organic layer was dried, filtered, and concentrated. Column chromatography (1:10 ether/pentane) on silica gel afforded the acyloxyfurans as oils.

The intermediate furan prepared which corresponds to the general formula previously presented is 2-Acetoxy-5-methylfuran: It is a colorless oil and was prepared at a 40% yield. Infrared analysis and nuclear magnetic resonance analysis confirmed the preparation of the intermediate acyloxy furan oil.

Thereafter, the second step rearrangement was conducted utilizing boron trifluoride etherate as the Lewis acid. In particular, to a solution of the 2-acetoxy-5-methylfuran (1.75 mmol in four milliliters of benzene) at $0°$ C. was added 1.75 mmol of distilled boron trifluoride etherate. The solution was allowed to warm slowly to room temperature and stirred until thin layer chromotography indicated that the reactant had been consumed (4–20 h). The solution was then diluted with ether washed with sodium bicarbonate and brine, dried and concentrated. The crude product was filtered through silica gel to afford pure product. The pure product was 5-Acetyl-5-methyldihydro-2(5H)-furanone which is a novel ketolactone having the formula:

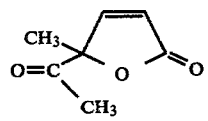

The presence of 5-acetyl-5-methyldihydro-2(5H)-furanone was confirmed with the following technical data: boiling point $65°$ C., IR(film)1780 , 1725, 1600 cm$^{-1}$; NMR (CDCl$_3$) $\gamma$1.61 (s, 3H), 2.20 (s, 3H) 6.20 (d, J=6 Hz 1H) 7.45 (d, J=6 HZ, 1H).

In addition quantitative analysis calculation for the emperical formula C$_7$J$_8$O$_3$ showed 59.99% carbon, 5.75% hydrogen and actual analysis revealed 59.88% carbon and 5.80% hydrogen which indicated within statistical accuracy the presence of the desired furanone.

This compound was tested and found to exhibit activity as a plant growth inhibitor.

In the above identified examples, substantially similar results are achieved if stannic chloride, aluminum chloride titanium tetrachloride, zinc chloride or boron trichloride are utilized as the Lewis acid.

EXAMPLE 2

The identical procedure of Example 1 was repeated utilizing the same angelicalactone as the starting butenolide. In this example the acid chloride used was hexanoyl chloride (R'''=C$_5$H$_{11}$). The same mmol quantities were used as used in Example 1. The intermediate acylated product prepared was 2-Hexanoyloxy-5-methylfuran: colorless oil, 40% yield; IR (film) 2964, 2940, 2880, 1780 cm$^{-1}$; NMR (CDCl$_3$) 0.7 −1.9 (m, 9H) 2.25 (d, 3H) 5.75 (d, 1H) 5194 (d of t, 1H).

The 2-hexanoyloxy-5-methylfuran after separation was utilized in the rearrangement second step of this invention utilizing boron trifluoride etherate in an equal molar quantity (1.75 mmol). To prepare a 40% yield of 5-hexanoyl-5-methyldihydro-2(5H)furanone. Reaction conditions were as specified in Example 1. The presence of the furanone product was confirmed by the following data: 40% yield: bp 77° C. (2 mm); IR (film) 2960, 2935, 2870, 1780, 1725, 1600 cm$^{-1}$; NMR (CDCl$_3$) 0.7−1.7 (m, 9H) 1.64 (s, 3H), 2.6 (m, 2H), 6.23 (d, J=6 HZ, 1H), 7.5 (d, J=6 HZ, 1H).

Analysis calculated for C$_{11}$H$_{16}$O$_3$: C, 67.32%; H 8.22% Found: C 65.70%, H, 8.20%.

EXAMPLES 3-4

(Thiophene Preparation)

The exact same procedure utilized in Example 1 was again used with the starting compounds being the appropriate thiophene analogs having the following formulas:

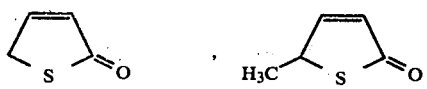

In both instances the starting thiophene analogs and the corresponding butenolides were acylated with acetyl chloride. In the first instance where R''' equals hydrogen, the resulting furan intermediate was:

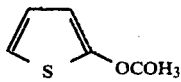

In the second instance, the resulting acylated intermediate furan was:

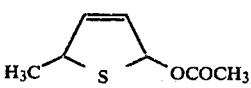

These thiophene furan ring containing compounds were then reacted in the exact same procedure mentioned in Example 1 with Lewis acid base boron trifluoride etherate to provide in the first instance: 5 acetyl thiophene-2-ol acetate, a 45% yield, having the formula:

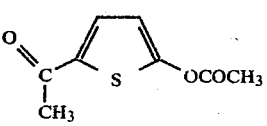

The analytical data for the compound is as follows: 5-Acetylthiophen-2-ol Acetate: 45% yield, mp. 103°-105° C.; IR (mull) 1775, 1660 cm$^{-1}$; NMR (CDCl$_3$) s 2.38 (s, 3H), 2.55 (s, 3H), 6.84 (d, J=4 Hz, 1H), 7.62 (d, J=4 HZ 1H). Analysis calculated for C$_8$H$_8$O$_3$S: C, 52.16%; H, 4.38% Found: C, 52.19%; H, 4.41%.

In the second instance where a methyl group appears on the ring at the gamma position, it has been found that the rearrangement occurs somewhat differently. Namely, the carbonyl group does not add at the gamma position but rather as at the alpha position to provide 3-acetyl-5-methylthiophen-2-ol: 40% yield, oil; IR (film) 1735, 1630 cm$^{-1}$; NMR (CDCl$_3$) s 2.26 (s, 6H), 6.26 (br s, 1H); high resolution mass spectrum, m/e 156.02327 (C$_7$H$_8$O$_2$S requires 156.02451) which confirms the formation of the compound.

Therefore, it can be seen that a useful synthesis has been provided to prepare novel keto lactones and in addition the appropriate thiophene analogs of the same. The novel arrangement is provided by use of Lewis acids to react with furan intermediates prepared by acylation of butenolides.

What is claimed is:

1. A method of preparing rearranged acyloxy furans and thiophenes from butenolides, comprising:

reacting a butenolide of the formula:

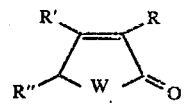

wherein R, R' and R'' are selected from the group consisting of hydrogen and non-functionally substituted alkyls, alkenyls, alkynyls and aryls, and W is selected from the group consisting of oxygen and sulfur with an acid and halide acylating agent of the formula:

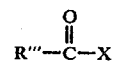

wherein R''' is selected from the same group as R, R' and R'' and X is a halide said reaction being conducted in an inert atmosphere and in the presence of a strong organic base and a suitable organic solvent for said base to provide an acylated furan ring containing intermediate;

separating said intermediate from other reaction materials; and thereafter reacting said acylated furan ring containing intermediate, in the presence of at least a catalytically effective amount of a lewis acid in an anhydrous solvent to provide a rearranged acyloxy furan or thiophene analog thereof.

2. The process of claim 1 wherein R, R', R'' and R''' are C$_1$ to C$_{12}$ substituents.

3. The process of claim 1 wherein said acid halide is an acid chloride.

4. The process of claim 1 wherein W is oxygen.

5. The process of claim 1 wherein said strong organic base is a dialkyl amide base.

6. The process of claim 1 wherein the process is conducted in an inert solvent.

7. The process of claim 1 wherein said Lewis acids are selected from the group consisting of boron trifluoride, stannic chloride, aluminum chloride, titanium tetrachloride, zinc chloride and boron trichloride.

8. The process of claim 1 wherein the amount of said Lewis acid is from about 10% of an equal molar quantity of said acylated furan ring containing intermediate up to an equal molar amount.

9. The process of claim 1 wherein said anhydrous solvent is a chloro carbon solvent.

* * * * *